United States Patent [19]

Palmer et al.

[11] 4,038,329

[45] July 26, 1977

[54] PROCESS FOR PURIFICATION OF NEOPENTYL GLYCOL

[75] Inventors: Billy W. Palmer; Howard N. Wright, Jr., both of Longview, Tex.

[73] Assignee: Eastman Kodak Company, Rochester, N.Y.

[21] Appl. No.: 632,759

[22] Filed: Nov. 17, 1975

[51] Int. Cl.² .............................................. C07C 29/24
[52] U.S. Cl. .................................. 260/637 P; 203/88; 203/43; 203/71
[58] Field of Search ..................................... 260/637 P

[56] References Cited

U.S. PATENT DOCUMENTS

| 3,504,042 | 3/1970 | Shimono et al. | 260/637 P X |
| 3,808,280 | 4/1974 | Merger et al. | 260/637 P X |

FOREIGN PATENT DOCUMENTS

| 44-10767 | 5/1969 | Japan | 260/637 P |
| 43-26283 | 11/1968 | Japan | 260/637 P |

Primary Examiner—Bernard Helfin
Attorney, Agent, or Firm—Edward R. Weber; Daniel B. Reece, III

[57] ABSTRACT

Neopentyl glycol is recovered from an impure process stream by the steps of (1) extracting neopentyl glycol from the impure stream with an organic solvent or mixture of solvents, (2) flashing the neopentyl glycol solvent mixture in a thermosiphoning reboiler so as to separate the solvent from the neopentyl glycol under atmospheric conditions, and (3) refining the neopentyl glycol by atmospheric distillation.

20 Claims, No Drawings

PROCESS FOR PURIFICATION OF NEOPENTYL GLYCOL

This invention relates to a process for the purification of neopentyl glycol. More particularly, this specification describes a process for the purification of neopentyl glycol without the necessity of using reduced pressure processes.

Crude neopentyl glycol when produced by the alkali catalyzed condensation of formaldehyde and isobutyraldehyde is usually contaminated with water, 2,2,4-trimethylpentanediol-1,3 and various alkali or alkali earth basic metal salts. The water is easily removed, but the basic metal salts present problems. Among the metal salts which may be present are alkali and alkaline earth metal hydroxides, carbonates, bicarbonates, salts of organic acids, and fines from the hydrogenation catalyst. In particular, neopentyl glycol rapidly decomposes at its atmospheric boiling point if the sodium content is much greater than 50 parts per million. Separating the neopentyl glycol from sodium salts by conventional methods requires distillation of the neopentyl glycol under reduced pressure or other expensive steps such as fractional crystallization.

Therefore, it is an object of this invention to purify neopentyl glycol without the necessity of using reduced pressure.

A further object of this invention is to purify neopentyl glycol without the necessity of using fractional crystallization or other expensive purification steps.

These and other objects of the invention will become apparent from the following description and the appended claims.

It has now been discovered that neopentyl glycol can be recovered from an impure neopentyl glycol containing stream at atmospheric pressure by the steps of (1) extracting the crude neopentyl glycol containing mixture with an organic solvent or mixture of solvents, (2) flashing the neopentyl glycol solvent mixture so as to separate the solvent from the neopentyl glycol, and (3) further refining the neopentyl glycol by atmospheric distillation.

The initial extraction step serves to remove neopentyl glycol from the water solution which contains trace amounts of organics and a significant amount of basic metal salts. Any of a number of solvents or solvent mixtures can be used. Suitable solvents include aliphatic or aromatic esters, ketones, alcohols, hydrocarbons, or mixtures thereof. Any solvent or combination of solvents which are water immiscible and can extract all or most of the neopentyl glycol while excluding all or most of the sodium salts may be utilized. In addition, the solvent must be readily separable from the neopentyl glycol. useful solvents include ketones and esters with boiling points between about 110° C. and 150° C., such as isobutyl acetate, isobutyl isobutyrate, propyl, butyl and amyl alcohols, and aliphatic and aromatic hydrocarbons with boiling points of between about 50° C. and 150° C. Preferred solvents are those which are either feeds or products of the process, such as isobutyraldehyde and isobutanol.

A particularly efficient hydroxylic solvent combination which has been discovered is a mixture of toluene and isobutanol. By "hydroxylic" we mean a solvent that contains at least one component with an alcoholic hydroxyl group. Toluene itself is a very inefficient extractant for aqueous neopentyl glycol while isobutanol removes both neopentyl glycol and the salts. The mixture of toluene and isobutanol is exceptionally efficient because it extracts essentially all of the neopentyl glycol and excludes most of the salts. In addition, the toluene isobutanol mixture lowers the boiling point of the resulting toluene/isobutanol/neopentyl glycol solution from about 210° C. to 155° C. The composition of the toluene/isobutanol solvent system can be varied from about 25 percent isobutanol to about 75 percent isobutanol, but a 50/50 mixture of toluene and isobutanol has been found to give the best balance of extractive properties versus salt carryover. It is quite surprising that a combination of solvents could be found which would not only separate 99 percent of the neopentyl glycol from the solution without extracting a significant portion of the salts but would lower the boiling point by 55° C. which is almost a 25 percent reduction in boiling point.

In one embodiment of the process of our invention the crude stream comprising water, neopentyl glycol, organic by-products of the manufacturing process, and sodium salts is introduced near the top of a countercurrent extraction column. The extracting solvent is introduced near the bottom of the column. The solvent-neopentyl glycol extract is removed from the top of the column and an aqueous phase containing substantially all the salts and some organic by-products is removed from the bottom of the column. The neopentyl glycol containing extract from the top of the extractor is passed to a decanter where any entrained water is removed and returned to the extractor. The organic overflow from the decanter is fed to the bottom of a thermosiphoning reboiler. Neopentyl glycol and solvent are stripped overhead from the thermosiphoning reboiler at 155° C. and atmospheric pressure. This step almost completely eliminates residual sodium from the remainder of the process. The neopentyl glycol vapor from the thermosiphoning reboiler is introduced near the middle of a solvent removal column wherein an atmospheric pressure separation is made between solvent and neopentyl glycol. Solvent removed overhead is returned to the extractor. The neopentyl glycol containing effluent from the base is passed to a purification column which is also operated at atmospheric pressure. This column produces specification grade (i.e., greater than 98.5% pure) neopentyl glycol as an overhead. Remaining organic by-products and any residual salts are removed as a base sludge. In the absence of 2,2,4-trimethylpentanediol-1,3 or other water insoluble high boilers the neopentyl glycol from the solvent removal column can be purified by flash distillation.

The neopentyl glycol stream leaving the thermosiphoning reboiler must contain less than about 0.5 parts per million sodium if an acceptable sludge rate is to be maintained in the subsequent purification distillation. This is necessary in order to maintain the total sodium content in the purification column at less than about 50 parts per million. If desired, additional water can be added near the top of the extraction column to help remove the sodium salts. Likewise, the thermosiphoning reboiler can be eliminated so long as the sludge rate of the purification column is sufficiently high to maintain the sodium content in the column at less than about 50 parts per million.

The process of the instant invention is illustrated in greater detail by the following examples. It is understood that these examples are not intended to limit the invention and obvious modifications will occur to those skilled in the art.

EXAMPLE 1

An extractor consisting of a 6-foot by 2-inch diameter Pyrex tube is set up. The solvent feed point is eight inches above the bottom outlet. The crude neopentyl glycol containing stream is fed three feet above the solvent feed point. A water backwash feed point is provided one foot above the crude feed point. Top overflow is 16 inches above the water feed point. The overflow from this column is introduced in the bottom of the heated side of a thermosiphoning reboiler. The vapor from the thermosiphoning reboiler is introduced at the midpoint of a solvent recovery solumn. The solvent recovery column is a 2-inch diameter glass column packed with ¼ inch perforated 316 stainless steel packing. There is a two foot packed section above the feed point and a two foot packed section below the feed point. The base take off from the solvent recovery column is introduced into a purification column. The purification column is a three foot by one inch column packed with Penn State 304 stainless steel packing.

For this example the feed rate to the extractor is 244.5 grams per hour. This feed contains, in additiion to neopentyl glycol, 45.8 percent water, 0.45 percent sodium hydroxide, and 1.54 percent sodium salts with an average molecular weight of 128. There is a trace of 2,2,4-trimethylpentanediol-1,3-present. A fresh water backwash is fed at 44.5 grams per hour. This fresh water feed is used in an attempt to wash the sodium salts out of the extract. The solvent used is 25 percent isobutanol and 75 percent toluene. The solvent is introduced at the solvent feed point at a rate of 1465 grams per hour. During a 40 hour run no material is sludged from the base of the thermosiphoning reboiler. Sludge at a rate of 1.17 percent is removed from the base of the product purification column. 98.6 Percent of the neopentyl glycol feed is isolated as pure neopentyl glycol. The extractor is operated at 60° C. The base temperature of the thermosiphoning reboiler is 155° C., that of the solvent removal column is 213° C., and that of the product purification column is 216° C. At the end of the run the base of the thermosiphoning reboiler contains 123 ppm. of sodium. The base of the product purification column contains 50–60 ppm. sodium.

EXAMPLE 2

The same equipment set up is used as described in Example 1. No fresh water is utilized as a backwash to the extractor. The solvent utilized in this run is 50/50 isobutanol/toluene by weight. The feed material contains 42.6 percent neopentyl glycol by gas chromotographic analysis. In addition to water, the feed material contains 0.5 percent sodium hydroxide and 1.5 percent sodium salts of an average molecular weight of 128. During an 88 hour run the ratio (by volume) of solvent to feed is 6.85. A sludge amounting to 0.5 percent by weight of the neopentyl glycol feed is removed from the base of the thermosiphoning reboiler and recycled to the extractor. 98.1 Percent of the neopentyl glycol fed to the system is recovered as specification grade material. A sludge rate of 1.1 percent is maintained at the bottom of the purification column. The sodium content in the base of the purification column is approximately 50 ppm. The final sodium content in the thermosiphoning reboiler is about 3300 parts per million. Sodium content in the thermosiphoning reboiler can be controlled by recycling a sludge stream from the reboiler to the extractor. There was no indication of decomposition of the neopentyl glycol in any part of the process.

EXAMPLE 3

The general procedure of Example 1 is followed except no thermosiphoning reboiler is used and the extract from the extractor is introduced at the feed point of the solvent recovery column. A sludge rate of 4 percent is necessary at the base of the product purification column to keep the sodium content below 60 parts per million. This sludge can be returned to the extractor if no significant quantity of high boilers are present. If significant quantities of high boilers are present, they must be purged to prevent a build up in the system through constant recycling through the extractor. This simplified procedure will work as efficiently as the system of Example 1 and 2 if the neopentyl glycol stream is free of water insoluble high boilers such as 2,2,4-trimethylpentanediol-1,3.

The invention has been described in detail with particular reference to preferred embodiments thereof, but it will be understood that variations and modifications can be effected within the spirit and scope of the invention as described hereinabove and in the appended claims.

We claim:

1. A process for the purification of crude neopentyl glycol produced by the alkali catalyzed condensation of formaldehyde and isobutyraldehyde consisting of the following steps:
   A. extraction of crude neopentyl glycol with a hydroxylic organic solvent or mixture of solvents selected from the group consisting of alcohols and aliphatic and aromatic hydrocarbons having boiling points of between about 50° C. and about 150° C. which solvent or mixture of solvents has the property of being a solvent for neopentyl glycol and a nonsolvent for metal salts,
   B. separating the neopentyl glycol/organic solvent extract into a solvent stream and a neopentyl glycol stream by distillation under atmospheric conditions,
   C. purifying the neopentyl glycol stream under atmospheric conditions.

2. A process as in claim 1 in which the solvent consists of a mixture of toluene and isobutanol.

3. A process as in claim 2 wherein the solvent consists of from about 25% toluene/75% isobutanol to about 75% toluene/25% isobutanol.

4. A process according to claim 3 wherein the solvent consists of a mixture of about 50% toluene and about 50% isobutanol.

5. The process according to claim 1 wherein the separation of the neopentyl glycol/solvent extract into a neopentyl glycol containing stream and a solvent stream is accomplished by introducing the neopentyl glycol/solvent extract into the base of the heated leg of a thermosiphoning reboiler and the subsequent introduction of the vapors from the thermosiphoning reboiler into an distillation column operated at atmospheric pressure.

6. A process according to claim 1 wherein the purification of the neopentyl glycol is accomplished by introducing the neopentyl glycol containing stream obtained from step (B) into a distillation column operated at atmospheric pressure.

7. A process for the purification of a crude neopentyl glycol stream comprising neopentyl glycol, water, 2,2,4-trimethylpentanediol-1,3 and various alkali or alkali earth basic metal salts which consists of the following steps:
   A. extraction of crude neopentyl glycol with a hydroxylic organic solvent or mixture of solvents selected from the group consisting of alcohols and aliphatic and aromatic hydrocarbons having boiling points of between about 50° C. and about 150° C. which solvent or mixture of solvents has the property of being a solvent for neopentyl gylcol and a nonsolvent for metal salts,
   B. flashing the neopentyl glycol solvent mixture in a thermosiphoning reboiler followed by atmospheric distillation to separate the neopentyl glycol and the solvent,
   C. atmospheric distillation of the neopentyl glycol.

8. A process as in claim 7 in which the solvent consists of a mixture of toluene and isobutanol.

9. A process as in claim 8 wherein the solvent consists of from about 25% toluene/75% isobutanol to about 75% toluene/25% isobutanol.

10. A process according to claim 9 wherein the solvent consists of a mixture of about 50% toluene and about 50% isobutanol.

11. A process for the purification of crude neopentyl glycol produced by the alkali catalyzed condensation of formaldehyde and isobutyraldehyde consisting of the following steps:
   A. extraction of crude neopentyl glycol with a mixture of solvents consisting of an alcohol and an aliphatic or aromatic hydrocarbon having a boiling point between about 50° C. and about 150° C. which solvent mixture has the property of being a solvent for neopentyl glycol and a nonsolvent for metal salts,
   B. separating the neopentyl glycol/organic solvent extract into a solvent stream and a neopentyl gylcol stream by distillation under atmospheric conditions,
   C. purifying the neopentyl glycol stream under atmospheric conditions.

12. A process as in claim 11 in which the solvent consists of a mixture of toluene and isobutanol.

13. A process as in claim 12 wherein the solvent consists of from about 25% toluene/75% isobutanol to about 75% toluene/25% isobutanol.

14. A process according to claim 13 wherein the solvent consists of a mixture of about 50% toluene and about 50% isobutanol.

15. A process according to claim 11 wherein the separation of the neopentyl glycol/solvent extract into a neopentyl glycol containing stream and a solvent stream is accomplished by introducing the neopentyl glycol/solvent extract into the base of the heated leg of a thermosiphoning reboiler and the subsequent introduction of the vapors from the thermosiphoning reboiler into a distillation column operated at atmospheric pressure.

16. A process according to claim 11 wherein the purification of the neopentyl glycol is accomplished by introducing the neopentyl glycol containing stream obtained from step (B) into a distillation column operated at atmospheric pressure.

17. A process for the purification of a crude neopentyl glycol stream comprising neopentyl glycol, water, 2,2,4-trimethylpentanediol-1,3 and various alkali or alkali earth basic metal salts which consists of the following steps:
   A. extraction of crude neopentyl glycol with a mixture of solvents consisting of an alcohol and an aliphatic or aromatic hydrocarbon having a boiling point between about 50° C. and about 150° C. which solvent mixture has the property of being a solvent for neopentyl glycol and a nonsolvent for metal salts,
   B. flashing the neopentyl glycol solvent mixture in a thermosiphoning reboiler followed by atmospheric distillation to separate the neopentyl gylcol and the solvent,
   C. atmospheric distillation of the neopentyl glycol.

18. A process as in claim 17 in which the solvent consists of a mixture of toluene and isobutanol.

19. A process as in claim 18 wherein the solvent consists of from about 25% toluene/75% isobutanol to about 75% toluene/25% isobutanol.

20. A process according to claim 19 wherein the solvent consists of a mixture of about 50% toluene and about 50% isobutanol.

* * * * *